United States Patent [19]

Kurimoto et al.

[11] Patent Number: 5,672,692
[45] Date of Patent: Sep. 30, 1997

[54] PURIFICATION OF HUMAN MYELOMONOCYTE INTERFERON GAMMA WITH AN IMMOBILIZED ANTIBODY

[75] Inventors: Masashi Kurimoto; Masakazu Mitsuhashi, both of Okayama, Japan

[73] Assignee: Kabushiki Kaisha Hayashibara Seibutsu Kagaku Kenkyujo, Okayama, Japan

[21] Appl. No.: 625,369

[22] Filed: Apr. 1, 1996

Related U.S. Application Data

[62] Division of Ser. No. 476,040, Jun. 7, 1995, Pat. No. 5,554,515, which is a division of Ser. No. 336,224, Nov. 7, 1994, Pat. No. 5,518,899, which is a division of Ser. No. 62,323, May 17, 1993, Pat. No. 5,362,490, which is a continuation of Ser. No. 658,740, Feb. 22, 1991, abandoned, which is a continuation-in-part of Ser. No. 78,005, Jul. 21, 1987, abandoned, and Ser. No. 379,318, Jul. 13, 1989, abandoned.

[30] Foreign Application Priority Data

| Jul. 25, 1986 | [JP] | Japan | 61-176266 |
| May 25, 1987 | [JP] | Japan | 62-125777 |
| Jul. 23, 1988 | [JP] | Japan | 63-184069 |

[51] Int. Cl.⁶ ............ C07K 3/20; C07K 17/00; C12P 21/04; G01N 33/53
[52] U.S. Cl. ............ 530/413; 424/85.5; 435/70.21; 435/70.5; 435/240.2; 435/240.26; 436/518; 436/548; 530/351
[58] Field of Search ............ 435/70.21, 70.5, 435/240.26, 240.2; 424/85.1, 85.5, 85.2; 530/351, 413; 436/548

[56] References Cited

U.S. PATENT DOCUMENTS

| 4,791,101 | 12/1988 | Adolf | 514/2 |
| 4,939,178 | 7/1990 | Muller | 514/729 |
| 4,946,674 | 8/1990 | Von Eichburn et al. | 424/85.5 |
| 5,407,811 | 4/1995 | Montagnier et al. | 435/70.21 |
| 5,422,239 | 6/1995 | Wands et al. | 435/5 |

FOREIGN PATENT DOCUMENTS

| 3423234 | 2/1986 | Germany. |
| 60-64999 | 4/1985 | Japan. |

OTHER PUBLICATIONS

Miyata et al, *J. Biochem.*, 99, 1681–1688 (1987).
Braude, *Biochemistry*, 23, 5603–5609 (1984).
Gray et al, *Nature*, 295, 503–508 (1982).
Devos et al, *J. Interferon Res.*, 4, 461–468 (1984).
Yamamoto et al, Studies on the Sugar Chains of Interferon from Human Peripheral–Blood Lymphocytes, *J. Biochem.*, 105:1034–1039 (1989).

*Primary Examiner*—David M. Naff
*Attorney, Agent, or Firm*—Browdy and Neimark

[57] ABSTRACT

A human myelomonocyte interferon-gamma having a novel polypeptide and carbohydrate chain structure is produced by propagation of an established human myelomonocyte in vitro or after being implanted in a non-human warm-blooded animal or in a diffusion chamber placed inside or outside the body of the animal. The human myelomonocyte may be contacted with an inducer during propagation. A monoclonal antibody specific to the human myelomonocyte interferon-gamma is produced by immunizing a non-human warm-blooded animal with purified human myelomonocyte interferon-gamma as an antigen, recovering an antibody producing cell from the animal and fusing the cell with a myeloma cell to produce a hybrid capable of producing the monoclonal antibody. The human myelomonocyte interferon-gamma can be purified by chromatography with an immobilized anti-human myelomonocyte interferon-gamma antibody such as the monoclonal antibody. The human myelomonocyte interferon-gamma can be used as a prophylactic and therapeutic agent for human interferon-gamma susceptive diseases.

5 Claims, 2 Drawing Sheets

PURIFICATION OF HUMAN MYELOMONOCYTE INTERFERON GAMMA WITH AN IMMOBILIZED ANTIBODY

This is a division of parent application Ser. No. 08/476,040, filed Jun. 7, 1995, now U.S. Pat. No. 5,554,515, which is a division of application Ser. No. 08/336,224, filed Nov. 7, 1994, now U.S. Pat. No. 5,518,899, which is a division of application Ser. No. 08/062,323, filed May 17, 1993, now U.S. Pat. No. 5,362,490, which is a continuation of application Ser. No. 07/658,740, filed Feb. 22, 1991, now abandoned, which is a continuation-in-part of application Ser. No. 07/078,005, filed Jul. 21, 1987, now abandoned, and also a continuation-in-part of application Ser. No. 07/379,318, filed Jul. 13, 1989, now abandoned.

BACKGROUND OF THE INVENTION

1. Field of the invention

The present invention relates to a novel human myelomonocyte interferon-gamma, a process to prepare said interferon-gamma, and its use.

More particularly, the present invention relates to a novel human myelomonocyte interferon-gamma, and a process for preparing said interferon-gamma, characterized by allowing an established human myelomonocyte capable of producing myelomonocyte interferon-gamma to produce said interferon-gamma, and recovering the accumulation; a process to prepare a monoclonal anti-interferon-gamma antibody using the same; and a method for purifying said interferon-gamma using the monoclonal antibody, as well as to a prophylactic and therapeutic agent for interferon-gamma susceptive disease containing the human myelomonocyte interferon-gamma as an effective ingredient.

2. Description of the Prior Art

As described in Shigeyasu Kobayashi, "Interferon", published by Kodansha Co., Ltd., Tokyo, Japan (1975), D. A. J. Tyrrell, "Interferon and its Clinical Potential", published by William Heinemann Medical Books Ltd., London (1976), and *Protein, Nucleic Acid and Enzyme*, Vol.21, No.4, pp.245-333 (1976), interferon is a name to designate glycoproteins that are extracellularly inducible in viable cell by subjecting it to the action of an interferon inducer, for example, virus, bacterium, protozoon, rickettsia, nucleic acid, endotoxin and polysaccharide, as well as having an activity of nonspecifically inhibiting viral growth.

This activity has rendered interferons since the discovery a potential prophylactic and therapeutic agent for vital diseases. Recent studies revealed that interferons exert an antioncotic activity on vital tumors, as well as on nonviral tumors. Because of the activity, the development of pharmaceuticals using interferons is in great expectation.

Interferons include interferon-alpha (or leukocyte interferon), interferon-beta (or fibroblast interferon), and interferon-gamma (or immune interferon). Preparation of interferon-alpha and interferon-beta has been established by using leukocyte and fibroblast cell. Recently, pharmaceuticals incorporated with these interferons have been commercialized.

Respective interferon will hereinafter be abbreviated as "IFN-alpha", "IFN-beta" and "IFN-gamma" occasionally with the prefix "Hu" representing human origin.

Although various methods have been proposed for preparing HuIFN-gamma, no method has been practiced on industrial scale.

The methods using leukocyte or T lymphocyte derived from human peripheral blood, as proposed, for example, in Japanese Patent Laid-Open Nos. 58,891/82, 82,092/84, 70,099/85, 87,300/85, 139,700/85 and 149,600/85, International Patent Publication in Japanese Nos. 500,961/82 and 502,032/83, are practically unfavorable because an ample supply of the material cell is very difficult and the HuIFN producibility of these cells is insufficient.

Japanese Patent Laid-Open No. 98,118/80 proposes the method wherein a human cell, obtained by implanting an established human cell in a non-human warm-blooded animal or placing the cell in a diffusion chamber provided inside or outside the body of a non-human warm-blooded animal, and allowing the cell to proliferate while allowing the cell to receive the nutrient body fluid from the animal, is used in preparing HuIFN-gamma. This method is characterized by an ample supply of the material human cell.

We found that the HuIFN-gamma productivity of the method varies with the type of the human cell used. Thus, the method has room for improvement in preparing consistently high-titered HuIFN-gamma to be practiceable on an industrial scale.

It is known that HuIFN-gamma is much more stronger in cytostatic and antioncotic activities than HuIFN-alpha and HuIFN-beta. Also is known that combination with HuIFN-alpha and/or HuIFN-beta augments the antiviral, cytostatic and antioncotic activities of HuIFN-gamma. For these reasons, development of an industrial-scale preparation of HuIFN-gamma has been in great demand.

SUMMARY OF THE INVENTION

In view of the foregoing, we screened various established human cells, specifically, established human lymphoblastoid cells, for their HuIFN-gamma producibility that may facilitate industrial-scale preparation of HuIFN-gamma, as well as investigating the potentiality as prophylactic and therapeutic agent for HuIFN-gamma susceptive diseases.

As a result, we unexpectedly found that established human myelomonocytes exert a higher HuIFN-gamma producibility than other lymphoblastoid cells, and are suitable for HuIFN-gamma producer cell, as well as that the obtained HuIFN-gamma is a novel HuIFN-gamma because of its polypeptide and carbohydrate chain structures, and that the obtained human myelomonocyte IFN-gamma is superiorly efficacious when used in prophylactic and therapeutic agent for HuIFN-gamma susceptive diseases.

DETAILED DESCRIPTION OF THE INVENTION

Figure 1:
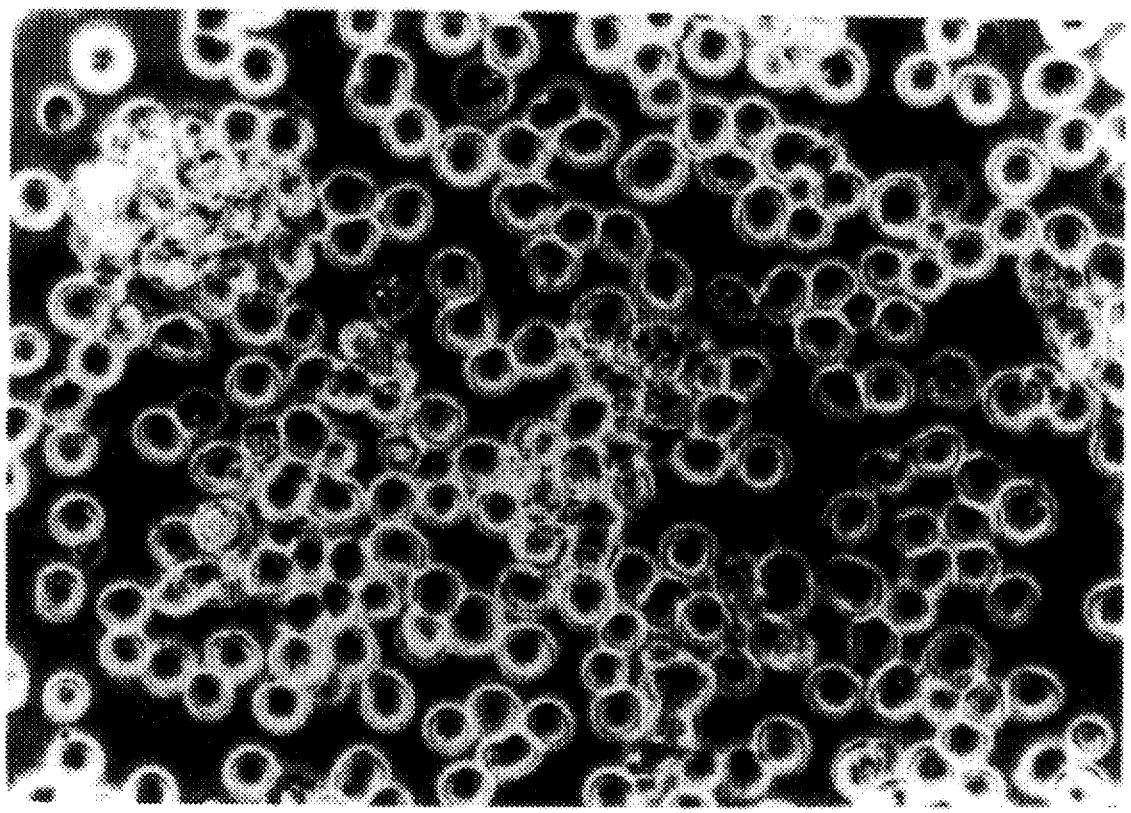
FIG. 1 is the phase-contrast microscopic view of HBL-38 cell.

The wording "established human myelomonocyte" means those which are not grouped into T and B cells and identifiable by checking the presence of myelomonocytic antigen by antigen-antibody reaction; for example, those as described in *Iwanami Koza Men-eki Kagaku* (*The Iwanami Immunology Series*), Vol.3, "Immunity responsive cells", edited by Tadamitsu Kishimoto and Takeshi Watanabe, pp.181-204, published by Iwanamishoten Publisher, Tokyo, Japan (1986), and "Mammalian Cell Culture Technology", written by Mikio Shikita and Isao Yamane, pp.141-162, published by Soft Science Publications, Tokyo, Japan (1985).

Examples of such myelomonocyte include HBL-38 cell established by us; HL-60 cell (ATCC CCL 240), KG-1 cell (ATCC CCL 246), ML-1 cell, ML-2 cell, ML-3 cell, THP-1 cell (ATCC TIB 202) and U-937 cell (ATCC CRL 1593) as described in the above references; and CTV-1 cell as reported in *Japanese Journal of Cancer Research (Gann)*, Vol.75, pp.660–664 (1984). Particularly, HBL-38 cell is most favorable in practicing the present invention because it exerts a higher human myelomonocyte IFN-gamma producibility. In order to augment the proliferation rate and human myelomonocyte IFN-gamma producibility, the gene coding human myelomonocyte IFN-gamma production can be introduced into a readily subculturable established human cell by cell fusion using, for example, polyethylene glycol or Sendai virus, or by gene recombinant technique using DNA ligase, restriction enzyme (nuclease) and DNA polymerase. If necessary, the human myelomonocyte IFN-gamma can be advantageously prepared by employing a method wherein a human myelomonocyte IFN-gamma polypeptide chain, which is prepared by a recombinant microorganism such as recombinant *E. coli*, or, by organic and chemical synthesis, or biochemical synthesis, is subjected, for example, to the action of a glycosyl transferase to transfer a carbohydrate chain to the polypeptide chain in a biochemical manner.

Proliferation method for human myelomonocyte can be suitably selected. Examples of such method include the tissue culture method wherein human myelomonocyte is inoculated on a nutrient culture medium and cultured in vitro; and the method wherein human myelomonocyte is implanted in a non-human warm-blooded animal or a diffusion chamber placed inside or outside the body of a non-human warm-blooded animal, and then allowed to proliferate while receiving the nutrient body fluid from the animal.

First, the in vitro proliferation will be explained.

In the in vitro proliferation, any nutrient culture medium can be used as long as human myelomonocyte proliferates therein, for example, RPMI 1640 medium and Eagle's minimal essential medium. These culture media may be modified by supplementing it with vitamin, mineral, carbohydrate, amino acid and/or mammalian serum.

The culture may be a monolayer or suspension culture. The temperature is about 20°–40° C., desirably, about 35°–38° C., and the inoculum should have a cell number per ml culture medium that attains a maximum proliferation over a period of about one week, preferably, about $10^4$–$10^7$ cells/ml culture medium.

The culture medium containing human myelomonocyte is cultured under these conditions for about 4–10 days, and, during the culture, the culture medium may be successively refreshed to supplement sufficient amounts of nutrients, as well as to wash and/or dilute the metabolites released in the culture medium.

The in vivo proliferation is now explained.

The human myelomonocytes can be easily proliferated with the in vivo proliferation by implanting it in a non-human warm-blooded animal or placing it in a diffusion chamber in which the cell can be supplied with the nutrient body fluid of the animal, and feeding the animal in usual manner. The in vivo proliferation attains a larger amount of human myelomonocyte IFN-gamma with no or much less nutrient culture medium containing expensive serum than in vitro tissue culture.

The in vivo proliferation has the additional advantages that it reduces cares during cell proliferation; that it stabilizes cell proliferation; and that it augments human myelomonocyte IFN-gamma producibility per cell, particularly, two- to ten-folds or more.

The non-human warm-blooded animals usable in the in vivo proliferation are those wherein human myelomonocytes proliferate, for example, fowls such as chicken and pigeon, and mammals such as dog, cat, monkey, goat, pig, cow, horse, rabbit, guinea pig, rat, hamster, mouse and nude mouse.

Since implantation of human myelomonocyte may elicit an undesirable immunoreaction in the animal, the use of an animal in the youngest possible stage, for example, egg, embryo or fetus, or newborn or infant animal, is desirable in order to reduce the immunoreaction to the lowest possible level.

For the same purpose, the animal may be irradiated with x-ray or gamma-ray, about 200–600 rem, or injected with an antiserum or an immunosuppressant prior to implantation.

When nude mouse is used, human myelomonocyte can be implanted without pretreatment and proliferated readily with less fear of causing undesirable immunoreaction because nude mouse elicits less immunoreaction even in adulthood.

One can stabilize cell proliferation and/or augment human myelomonocyte IFN-gamma production by successive implantation using the same or different non-human warm-blooded animals. These can be attained by, for example, first implanting and proliferating human myelomonocyte in hamster, then successively implanting the proliferated cell in nude mouse. Such implantation can be carried out with non-human warm-blooded animals of the same class or order, as well as those of the same species or genus.

Human myelomonocyte can be implanted in any site of the animal as long as the cell proliferates in the site: for example, in the allantoic cavity, intravenously, intraperitoneally or subcutaneously.

Alternatively, human myelomonocyte can be proliferated by placing it in conventional diffusion chamber of various shapes and sizes, equipped with an appropriate means which excludes the animal cell but supplies to HBL-38 the nutrient body fluid from a non-human warm-blooded animal, for example, membrane filter, ultrafilter or hollow fiber, pore size of about $10^{-7}$–$10^{-5}$ m; embedding, for example, intraperitoneally, the chamber in a non-human warm-blooded animal; and allowing the cell to proliferate in the chamber while allowing the cell to receive the nutrient body fluid from the animal.

The diffusion chamber can be arranged and placed, for example, on the animal, in such manner that the nutrient fluid in the diffusion chamber can freely circulate therethrough. The diffusion chamber can be arranged in such manner that the culture can be observed during the cell proliferation through the chamber wall, and/or that a diffusion chamber can be replaced at intervals with a fresh one to continue the cell proliferation over the life span of the animal without sacrifice, as well as to augment much more the cell production per animal.

Since in the method using diffusion chamber human myelomonocyte never contacts with the animal cell and elicits much less undesirable immunoreaction, any non-human warm-blooded animal can be freely used without pretreatment to reduce immunoreaction and the proliferated cell can be easily recovered.

The animal is fed in usual manner, and no special care is required even after implantation. The period for maximum cell proliferation is usually from 1–10 weeks. The number of the obtained myelomonocyte is about $10^7$–$10^{12}$ cells per animal or more. More particularly, according to the invention, the implanted myelomonocyte increases about $10^2$–$10^7$-fold or more, which is about $10$–$10^6$-folds or higher than that attained by inoculating and proliferating myelomonocyte on in vitro nutrient culture medium. This is very favorable in preparing human myelomonocyte IFN-gamma.

Any induction method can be employed in the invention as long as it induces human myelomonocyte IFN-gamma production in the human myelomonocytes obtained in this way. The human myelomonocyte can be exposed to the action of IFN-gamma inducer in the animal used for proliferation. For example, a human myelomonocyte proliferated in ascite in suspension, or a tumor, formed, for example, subcutaneously, is exposed directly to IFN-gamma inducer, and the resultant human myelomonocyte IFN-gamma is recovered from the ascite, serum and/or tumor, followed by purification.

The proliferated human myelomonocyte can be recovered from the animal, and then exposed in vitro to IFN-gamma inducer. For example, a human myelomonocyte obtained by recovery from ascite, or extraction and disaggregation of the tumor mass formed, for example, subcutaneously, is suspended in a nutrient culture medium kept at about 20°–40° C. to give a cell density of about $10^5$–$10^8$ cells/ml, and exposed to IFN-gamma inducer, followed by recovery and purification of the resultant human myelomonocyte IFN-gamma.

When diffusion chamber is used, human myelomonocyte can be exposed to IFN-gamma inducer in the diffusion chamber or after recovery therefrom.

The priming method using HuIFN and/or the superinduction method using antimetabolite can be employed to further augment the production of human myelomonocyte IFN-gamma.

Production of human myelomonocyte IFN-gamma per animal may be still further augmented by employing one or more of the following methods:

(1) a method wherein human myelomonocyte is exposed to IFN-gamma inducer in the animal, recovered from certain site of the animal or its whole body, and exposed in vitro to IFN-gamma inducer, (2) a method wherein human myelomonocyte is repeatedly exposed to IFN-gamma inducer, and (3) a method wherein the diffusion chamber embedded in or connected to the animal is replaced at intervals with a fresh chamber.

The IFN-gamma inducers usable in the invention are usually mitogens, for example, phytohemagglutinin, concanavalin A, pokeweed mitogen, lipopolysaccharide, endotoxin, lipid A, polysaccharide and bacterium.

Antigens act on sensitized cell as IFN-gamma inducer. The IFN-gamma inducers are usually used at a concentration of from about 0.001 µg/ml to 10 mg/ml. Combination with IFN-alpha inducer, for example, virus, nucleic acid and polynucleotide, may lead to an augmented production of human myelomonocyte IFN-gamma and/or induction of a simultaneous production of HuIFN-alpha.

The obtained human myelomonocyte IFN-gamma can be recovered with one or more conventional purification and separation methods, for example, salting-out, dialysis, filtration, centrifugation, concentration and lyophilization. When further purification is required, one or more other conventional procedures, for example, adsorption and desorption with ion exchange, gel filtration, isoelectric point fractionation, electrophoresis, ion exchange chromatography, high-performance liquid chromatography, column chromatography and affinity chromatography, are used in combination. Chromatography using monoclonal antibody leads to a human myelomonocyte IFN-gamma of the highest purity, i.e. up to about $10^8$ units/mg protein, and usually, $1\times10^7$–$3\times10^7$ units/mg protein.

The human myelomonocyte IFN-gamma thus obtained can be advantageously used in preventing and treating HuIFN-gamma susceptive diseases.

The wording "HuIFN-gamma susceptive diseases" means those which can be prevented or treated with human myelomonocyte IFN-gamma, for example, vital diseases such as epidemic conjunctivitis, herpetic keratitis, influenza, rubella, serum hepatitis, and acquired immune deficiency syndrome (AIDS); and nonviral diseases including malignant tumors such as colon carcinoma, lung carcinoma, liver carcinoma and osteosarcoma, and immunopathies including atopic allergy, myoasthenia, collagenosis, pernicious anemia, articular rheumatism, and systemic lupus erythematosus.

The agent according to the invention can be prepared into an appropriate form to meet the final uses, for example, into nebula, collyrium, collutory, a liquid medicine such as injection, a paste medicine such as ointment, and solid medicines such as powder, granule and tablet.

The human myelomonocyte IFN-gamma content is usually in the range of 1–10,000,000 units/g. The efficacy can be augmented by combining one or more lymphokines such as HuIFN-alpha, HuIFN-beta, tumor necrosis factor (TNF), lymphotoxin, interleukin 2, and B-cell differentiating factor, or natural or synthetic chemotherapeutic(s).

The human myelomonocyte IFN-gamma can be used in combination with adjuvant, filler and/or stabilizer. The agent thus obtained is suitable, for example, for antiviral agent, an antioncotic, an enhancer for antioncotic, depressant for metastasis of malignant tumor, a suppressant for palindromia, an immunoregulator, a therapeutic agent for rheumatism, and a therapeutic agent for immunopathy.

The activity of HuIFN was determined with the plaque reduction method using FL cell derived from human amnion as described in *Protein, Nucleic Acid and Enzyme*, Vol.20, No.6, pp.616–643 (1975).

The activity of HuIFN-gamma was determined after neutralization of HuIFN-alpha and HuIFN-beta respectively with anti-HuIFN-alpha- and anti-HuIFN-beta-antibodies.

The hemagglutination titer was determined in accordance with the method as described in J. E. Salk, *The Journal of Immunology*, Vol.49, pp.87–98 (1944).

HBL-38 cell established by us will hereinafter be described.

After culturing on in vitro nutrient culture medium, a leukocyte from an acute myeloleukemia patient (55-year old) began proliferation on the 21st day. We repeatedly subcultured the leukocyte and eventually succeeded to stably proliferate one of the subcultures. We named the subculture as "HBL-38".

(1) Proliferation Doubling time on RPMI 1640 medium supplemented with 10 v/v % fetal calf serum was about 30 hours.

(2) Morphology HBL-38 cell tended to attach on the inside bottom of flask during proliferation, but the attachment was loose and the cell was easily detachable. Although cell clumps were formed during proliferation, they were not rigid and easily disaggregated. The result of phase-contrast microscopic observation was as shown in FIG. 1. The cell was regularly rounded with a thickness of about 15 micrometers. The Giemsa's stain revealed that the nuclei was rounded occasionally with an irregular lobation or a karyolobism.

(3) Chromosome number Chromosome analysis was carried out with cells in exponential growth. The frequency distribution of chromosome numbers was as shown in Table I. Observation on 150 chromosomes revealed that the chromosome numbers were in a low diploid region and the most frequent distribution was 45 (53 chromosomes). Forty-two cells had a chromosome number of 44.

TABLE I

Frequency distribution of chromosome number

| Chromosome number | 31 | 32 | 36 | 40 | 41 | 42 | 43 | 44 | 45 | 46 | 47 | 48 | 49 | 50 |
|---|---|---|---|---|---|---|---|---|---|---|---|---|---|---|
| Cell number | 1 | 1 | 1 | 1 | 7 | 6 | 11 | 42 | 53 | 14 | 7 | 5 | 1 | 0 |

Figure 2:
FIG. 2 shows the results of karyotypic analysis on HBL-38 cell.

(4) Karyotypic analysis The results of karyotypic analysis were as shown in FIG. 2. The sex chromosome was XY, and this was consistent with that of the cell source. One counterpart of chromosome 17 and the whole of chromosome 18 were lacked. It was found that a chromosome was inserted respectively in a short arm (p) of chromosome 5 and a long arm (q) of chromosome 12. An unidentifiable marker chromosome and a chromatid were observed.

(5) Cell surface character Identification of HBL-38 cell was carried out with various cell surface antibodies, and the results were as shown in Table II. Analysis using goat erythrocyte (E), erythrocyte amboceptor (EA) and erythrocyte amboceptor complement (EAC) revealed that EA formed 10% rosette but the others did not. Detection of surface immunoglobulins (SmIg) using six anti-human goat antibodies revealed that HBL-38 cell was negative to all the antibodies. Screening of surface markers using monoclonal antibodies revealed that 3A1, MCS-2, B3/25 and MY-9 exerted a relatively high positiveness but NU-T2, Leu-5, Leu-4, A-50, BA-2, OKI-1, NU-N1, B2, MO-1 and MO-2 were negative.

(6) Screening of EB virus determined nuclear antigen (EBNA) HBL-38 cell was screened for EBNA several times from an early stage of the establishment. The results revealed that HBL-38 cell was EBNA-negative.

(7) Colony formation on soft agar medium HBL-38 cell was tested for colony formation in 0.3% agar medium containing colony stimulating factor (CSF). Inverted-microscopic observation on the 14th day revealed the presence of a colony-forming myeloid cell. The frequency was 1 to 2%. No colony was formed when no CSF was added.

Based on these data, HBL-38 cell was grouped into myelomonocyte.

TABLE II

Marker profile

Surface markers (Standard)

| E | EA | EAC | | | SmIg | | |
|---|---|---|---|---|---|---|---|
| ∩ | 10 | 0 | κ | λ | α | δ | γ | μ |
| | | | 0 | 0 | 0 | 0 | 0 | 0 |

(Monoclonal antibody)

| NU-T2 | Leu-5 | Leu-4 | Leu-3a | A50 | 3A1 | Leu-2a | BA2 | NU-N1 | Tac | OKM-1 | MCS-1 |
|---|---|---|---|---|---|---|---|---|---|---|---|
| 0 | 0 | 0 | 10 | 0 | 90 | 10 | 0 | 0 | 10 | 10 | 20 |
| MCS-2 | MY-1 | MY-9 | MO-1 | CA-2-38 | MO-2 | B7/21 | OKI-1 | B3/25 | A3/10 | B2 | |
| 100 | 10 | 70 | 0 | 40 | 0 | 10 | 60 | 100 | 60 | 0 | |

Virus marker

EBV
-

Note: The values indicate positiveness (%).

The following Experiments 1 are illustrative of preparing human myelomonocyte IFN-gamma.

Experiment 1

Comparison of established human lymphoblastoid cells on HuIFN-gamma producibility Experiment 1—1

HuIFN production by in vitro proliferated cell

An established human lymphoblastoid cell was inoculated to RPMI 1640 medium (pH 7.2) supplemented with 20% fetal calf serum, and the mixture was cultured at 37° C. in usual manner. The resultant culture was washed with serum-free RPMI 1640 medium (pH 7.2), and then suspended with a fresh preparation of the same culture medium to $1 \times 10^6$ cells/ml.

The resultant cell suspension was added with about 10 μg/ml of lipopolysaccharide, and the mixture was kept at 37°

C. for two days to induce HuIFN production. The culture was centrifugally separated, and the supernatant was determined for total HuIFN and human IFN-gamma activities.

The results were as shown in Table III.

As evident from these data, we found that human myelomonocytes was HuIFN-gamma producible and the production was higher than those attained with the established human lymphoblastoid cells tested. HBL-38 cell was extremely high in HuIFN-gamma producibility.

TABLE III

| T cell | | | |
|---|---|---|---|
| CCRF-CEM | TALL-1 | MOLT-3 | KE-37 |
| below 100 | below 100 | below 100 | below 100 |
| B cell | | | |
| NALM-1 | KLM-2 | Namalwa | BALL-1 |
| below 20 | below 20 | below 20 | below 20 |
| Non T•non B cell | | | |
| KM-3 | NALL-1 | KOPN-K | BV-173 |
| below 20 | below 20 | below 20 | below 20 |
| Non L•non M cell | | | |
| K-562 | HEL | SPI-801 | L-428 |
| below 20 | below 20 | below 20 | below 20 |
| Myelomonocyte | | | |
| HBL-38 | | KG-1 | |
| 3,800 (3,200) | | 1,600 (1,400) | |

Note: The values indicate HuIFN activity; and those in the parentheses, HuIFN-gamma activity.

Experiment 1-2

HuIFN production by in vivo proliferated cell

Newborn hamsters were injected with an antiserum prepared from rabbit in usual manner to weaken possible immunoreaction, implanted subcutaneously with an established human myelomonocyte, and fed for three weeks in usual manner. The tumor masses formed in the body of the hamsters were extracted and disaggregated by suspension in saline containing trypsin.

A suspension of the obtained cell was treated and determined for total HuIFN and HuIFN-gamma activities similarly as in Experiment 1—1.

The results were as shown in Table IV.

TABLE IV

| HuIFN production by myelomonocyte | |
|---|---|
| HBL-38 | KG-1 |
| 66,000 (59,000) | 31,000 (25,000) |

Note: The values indicate HuIFN activity; and those in the parentheses, HuIFN-gamma activity.

The data in Tables III and IV confirmed that established human myelomonocytes, specifically, HBL-38 cell, exerted a higher HuIFN-gamma producibility when proliferated in vivo than in vitro.

The following Examples are illustrative of preparing human myelomonocyte IFN-gamma.

EXAMPLE A-1

HBL-38 cell was inoculated on RPMI 1640 medium (pH 7.2), supplemented with 10 v/v % fetal calf serum, to $5 \times 10^5$ cells/ml.

The resultant mixture was cultured at 37° C. while periodically refreshing the culture medium. Thereafter, by using a fresh preparation of the same culture medium, the cell was washed and suspended to $2 \times 10^6$ cells/ml. The cell suspension was added with about 10 µg/ml of lipopolysaccharide, and the mixture was kept at 37° C. for two days to induce HuIFN production. The resultant culture was centrifugally separated to obtain a supernatant containing about 5,100 units of human myelomonocyte IFN-gamma per ml.

EXAMPLE A-2

Newborn hamsters were injected with an antiserum prepared from rabbit in usual manner to weaken possible immunoreaction, implanted subcutaneously with HBL-38 cell, and fed for four weeks in usual manner. The tumor masses, formed in the animals, about 20 g each, were extracted and disaggregated by suspension in saline containing collagenase.

After washing with Eagle's minimal essential medium, the cell was diluted with a fresh preparation of the same culture medium to about $2 \times 10^6$ cells/ml, and added with 200 µg/ml of phytohemagglutinin together with 5 g/ml of lipid A. The mixture was kept at 37° C. for two days to induce human myelomonocyte IFN production. The resultant culture was centrifugally separated to obtain a supernatant containing about 93,000 units of human myelomonocyte IFN-gamma. Thus, about 183,000,000 units of human myelomonocyte IFN-gamma was obtained per hamster.

EXAMPLE A-3

Newborn rats were intravenously implanted with KG-1 cell and fed for four weeks in usual manner.

The tumor masses, about 20 g each, formed in the animals, were extracted and disaggregated similarly as in Example A-2 to obtain a cell suspension. The cell suspension was added with about 100 hemagglutination titers/ml of Sendai virus and about 5 µg/ml of lipopolysaccharide, and the mixture was incubated at 37° C. for two days to induce human myelomonocyte IFN production. The resultant culture was centrifugally separated to obtain a supernatant containing about 49,000 units of human myelomonocyte IFN-gamma per ml. The human myelomonocyte IFN-gamma yield was about 97,000,000 units per rat.

EXAMPLE A-4

CTV-1 cell was suspended with saline in about 10 ml plastic cylindric diffusion chambers having a membrane filter, pore size of about 0.5 microns, and the diffusion chambers were embedded intraperitoneally in adult rats.

The rats were fed for four weeks in usual manner, and the chambers were removed.

The proliferated cell was treated similarly as in Example A-1 to induce human myelomonocyte IFN production. The resultant culture was centrifugally separated to obtain a supernatant containing about 41,000 units of human myelomonocyte IFN-gamma per ml. The yield was about 78,000,000 units per rat.

EXAMPLE A-5

Embryonated eggs prewarmed at 37° C. for one week were implanted with HBL-38 cell, and then incubated at this temperature for an additional one week. The proliferated cells were recovered by breaking the eggs and treated similarly as in Example A-2 to induce human myelomonocyte IFN production. The resultant culture was centrifugally separated to obtain a supernatant containing about 36,000 units of human myelomonocyte IFN-gamma per ml. The yield was about 60,000,000 units per 10 eggs.

The following Examples B are illustrative of preparing monoclonal anti-HuIFN-gamma antibody and of purifying human myelomonocyte IFN-gamma using the same.

EXAMPLE B-1(1)

Preparation of partially-purified human myelomonocyte IFN-gamma

A liquid containing human myelomonocyte IFN-gamma prepared by the method in Example A-2 was dialyzed against 0.01 M Tris-phosphate buffer (pH 8.5) for 20 hours, and then membrane-filtered. The filtrate was applied to an antibody column binding anti-HuIFN-alpha- and anti-HuIFN-beta-antibodies, and the non-adsorbed fraction was recovered. The fraction was chromatofocused to obtain a fraction with antiviral activity which was then concentrated and lyophilized to obtain a powder containing human myelomonocyte IFN-gamma in the activity yield of about 30%. The specific activity of the powder was about $10^6$ units/mg protein.

EXAMPLE B-1(2)

Preparation of monoclonal anti-HuIFN-gamma antibody

A partially-purified human myelomonocyte IFN-gamma obtained by the method in Example B-1(1) was dissolved saline to about 0.05 w/w %, and the resultant solution was added with an equivalent volume of Freund's complete adjuvant. Mice were injected intravenously with 0.2 ml aliquot of the mixture, and were on the 7th day after the first injection boosted similarly as above to effect immunization. The spleens wherein anti-HuIFN-gamma production had been induced in the antibody producing cell were extracted from the mice, minced and disaggregated, after which the spleen cell was suspended together with $P_3$-X63-Ag8 cell, a mouse myeloma cell purchased from Flow Laboratories Inc., Maryland, U.S.A., in 37° C. serum-free Eagle's minimum essential medium (pH 7.2) containing 50 w/v % polyethylene glycol 1000 to give respective cell density of $10^4$ cells/ml. Upon 5-minute standing, the cell suspension was diluted 20 times in a fresh preparation of the same culture medium, and the hybrid cells capable of growing on the hypoxanthine, aminopterin, thymidine containing medium were recovered and cloned in accordance with the method as reported in R. L. Davidson and P. S. Gerald, *Somatic Cell Genetics*, Vol.2, No.2, pp.175-176 (1976) to obtain a hybrid cell capable of producing anti-HuIFN-gamma antibody. The hybrid cell was then implanted intraperitoneally in mice in a dose of about $10^6$ cell per mouse, fed for two weeks and sacrificed. The body fluids recovered from the mice such as ascite and blood were centrifugally separated to obtain a supernatant which was then added with ammonium sulfate to 30–50% saturation. The resultant sediment was dialyzed and affinity-chromatographed with an immobilized HuIFN-gamma gel obtained by reacting at room temperature an HuIFN-gamma that had been obtained by the method in Example B-1(1) with BrCN-activated Sepharose. The obtained anti-HuIFN-gamma antibody fraction was dialyzed, concentrated and lyophilized into powder.

The product immunologically neutralized a human myelomonocyte IFN-gamma derived from human myelomonocyte.

The stability of the monoclonal antibody in aqueous solution was determined by measuring the residual neutralizing activity upon 30-minute incubation at pH 7.2. As the result, the monoclonal antibody retained over 80% activity when incubated at 60° C., but lost over 90% activity when incubated at 70° C. Upon 16-hour incubation at 4° C., the monoclonal antibody was found stable at a pH in the range of 4.0–11.0 but lost over 90% activity at pH 2.0.

Further investigation revealed that the monoclonal antibody was unstable in the presence of 2-mercaptoethanol and caused an antigen-antibody reaction specifically with anti-mouse immunoglobulin M antibody.

This confirmed that the monoclonal antibody was of class immunoglobulin M antibody.

EXAMPLE B-1(3)

Preparation of highly-purified human myelomonocyte IFN-gamma

A partially-purified human myelomonocyte IFN-gamma prepared by the method in Example B-1(1) was chromatographed on a column of an immobilized monoclonal antibody gel prepared by the method in Example B-1(2), and the fraction with human myelomonocyte IFN-gamma activity was recovered, dialyzed, concentrated and lyophilized to obtain a solid containing human myelomonocyte IFN-gamma in the yield of about 80%. The product was a highly-purified human myelomonocyte IFN-gamma, and the specific activity was about $1.5 \times 10^7$ units/mg protein.

EXAMPLE B-2

EXAMPLE B-2(1)

Preparation of partially-purified human myelomonocyte IFN-gamma

A solution containing a human myelomonocyte IFN-gamma prepared by the method in Example A-3 was partially purified in accordance with the method in Example B-1(1) to obtain a human myelomonocyte IFN-gamma preparation with a specific activity of about $10^6$ units/mg protein in the yield of about 20%.

EXAMPLE B-2(2)

Preparation of monoclonal anti-HuIFN-gamma antibody

Spleen cell was obtained by immunizing mice similarly as in Example B-1(2), except that the partially-purified human myelomonocyte IFN-gamma obtained in Example B-2(1) was used as the antigen.

The spleen cell was suspended together with P3-NS-1/1-Ag4-1 cell, a mouse myeloma cell purchased from Dainippon Pharmaceutical Co., Ltd., Osaka, Japan, in a salt solution containing 140 mM NaCl, 54 mM KCl, 1 mM $NaH_2PO_4$ and 2 mM $CaCl_2$ to respective cell density of $10^4$ cells/ml. To the cell suspension was added under ice-chilled conditions a fresh preparation of the same salt solution additionally containing an uv-irradiation inactivated Sendai virus, and the mixture was diluted about 20 times after a lapse of five minutes in 37° C. RPMI 1640 medium. A hybrid cell capable of producing anti-HuIFN-gamma antibody was cloned by treating the diluted mixture similarly as in Example B-1(2).

The obtained hybrid cell was implanted intraperitoneally in 7-day old hamsters whose immunoreaction had been weakened in usual manner in a dose of about $10^7$ cells per hamster, and the hamsters were treated similarly as in Example B-1(2) to obtain a monoclonal antibody.

The product immunologically neutralized a human myelomonocyte IFN-gamma derived similarly as the one prepared in Example B-1(2).

The stability of the monoclonal antibody in aqueous solution was determined by measuring the residual neutralizing activity upon 30-minute incubation at pH 7.2. As the result, the monoclonal antibody retained over 80% activity when incubated at 60° C., but lost over 90% activity when incubated at 70° C. Upon 16-hour incubation at 4° C., the monoclonal antibody was found stable at a pH in the range of 2.0–11.0.

Further investigation revealed that the monoclonal antibody was stable in the presence of 2-mercaptoethanol and caused an antigen-antibody reaction specifically with anti-mouse immunoglobulin G antibody.

This confirmed that the monoclonal antibody was of class immunoglobulin G antibody.

EXAMPLE B-2(3)

Preparation of highly-purified human myelomonocyte IFN-gamma

A partially-purified human myelomonocyte IFN-gamma prepared by the method in Example B-2(1) was chromatographed on a column of an immobilized monoclonal antibody prepared by the method in Example B-2(2), and the fraction containing human myelomonocyte IFN-gamma was recovered, dialyzed and concentrated to obtain a liquid containing human myelomonocyte IFN-gamma in the activity yield of about 85%. The product was a highly-purified human myelomonocyte IFN-gamma, and the specific activity was about $1.5 \times 10^7$ units/mg protein.

EXAMPLE B-3

A filtrate obtained by dialyzing a human myelomonocyte IFN-gamma containing supernatant, obtained by the method in Example A-1 was dialyzed against saline containing 0.01 M phosphate buffer (pH 7.2) for 15 hours, and membrane-filtering the resultant supernatant, was purified on an antibody column in accordance with the method in Example B-1(3), concentrated and lyophilized to obtain a solid containing human myelomonocyte IFN-gamma in the activity yield of about 75%. The product was a highly-purified human myelomonocyte IFN-gamma, and the specific activity was about $1.5 \times 10^7$ units/mg protein.

EXAMPLE B-4

A human myelomonocyte IFN-gamma containing supernatant obtained by the method in Example A-4 was dialyzed and membrane-filtered in accordance with the method in Example B-3. The resultant filtrate was purified on an antibody column and concentrated similarly as in Example B-2(3) to obtain a solution containing human myelomonocyte IFN-gamma in the activity yield of about 70%. The product was a highly-purified human myelomonocyte IFN-gamma, and the specific activity was about $1.5 \times 10^7$ units/mg protein.

EXAMPLE B-5

A human myelomonocyte IFN-gamma containing supernatant obtained by the method in Example A-5 was dialyzed and membrane-filtered in accordance with the method in Example B-3. The resultant filtrate was purified on an antibody column, concentrated and lyophilized similarly as in Example B-1(3) to obtain a solid containing human myelomonocyte IFN-gamma in the activity yield of about 70%. The product was a highly-purified human myelomonocyte IFN-gamma, and the specific activity was about $1.5 \times 10^7$ units/mg protein.

Experiment 2

Physicochemical properties of human myelomonocyte IFN-gamma

Experiment 2-1

Molecular weight of human myelomonocyte IFN-gamma

After feeding a highly-purified human myelomonocyte IFN-gamma, prepared by the method in Example B-1(3), to SDS-polyacrylamide gel electrophoresis in accordance with the method described by U. K. Laemmli, in *Nature*, Vol.227, pp.680–685 (1970), several bands were observed around the molecular weight of about 24,000, 20,000 and 16,000 daltons. The amounts of protein in the bands were about 7:2:1 based on their molecular ratios respectively. HuIFN-gamma activity was detected in each band. Furthermore, the presence of carbohydrate chains was checked by periodic acid Shiff base stain in accordance with the method described by R. A. Kapitany and E. J. Zebrowski, in *Analytical Biochemistry*, Vol.56, p.361–369 (1973), and the bands having a molecular weight of about 24,000 and about 20,000 daltons were determined positive.

Experiment 2-2

Amino acid sequence of human myelomonocyte IFN-gamma

The amino acid sequence of a highly-purified human myelomonocyte IFN-gamma, prepared by the method in Example B-1(3), was determined in accordance with the method described by Ernst Rinderknecht et al., in *The Journal of Biological Chemistry*, Vol.259, No.11, pp.6790–6797 (1984).

The human myelomonocyte IFN-gamma was digested with trypsin or V8 protease, a product of Sigma Chemical Company, St., Louis, Mo., U.S.A., and the resultant peptide fragments were fractionated with high-performance liquid chromatography. Each fragment was fed to "Model 470A", a gas-phase protein sequencer, commercialized by Applied Biosystems, Inc., California, U.S.A., and then analyzed with high-performance liquid chromatography to determine the amino acid sequence of human myelomonocyte IFN-gamma. Carbohydrate chains coupled to peptide fragments were first cut with glycopeptidase A, a product of Seikagaku Kogyo Kabushiki Kaisha, Tokyo, Japan, then fed to a gas-phase protein sequencer.

The evidence confirmed that the present human myelomonocyte IFN-gamma has a polypeptide chain shown by the following formula as the main structure:

Formula I:

```
    1                                           10
pyroGlu Asp Pro Tyr Val Lys Glu Ala Glu Asn Leu Lys Lys Tyr Phe 20                                       30
    Asn Ala Gly His Ser Asp Val Ala Asp Asn Gly Thr Leu Phe Leu 40
    Gly Ile Leu Lys Asn Trp Lys Glu Glu Ser Asp Arg Lys Ile Met 50                                       60
    Gln Ser Gln Ile Val Ser Phe Tyr Phe Lys Leu Phe Lys Asn Phe 70
    Lys Asp Asp Gln Ser Ile Gln Lys Ser Val Glu Thr Ile Lys Glu 80                                       90
    Asp Met Asn Val Lys Phe Phe Asn Ser Asn Lys Lys Lys Arg Asp 100
    Asp Phe Glu Lys Leu Thr Asn Tyr Ser Val Thr Asp Leu Asn Val 110                                      120
    Gln Arg Lys Ala Ile His Glu Leu Ile Gln Val Met Ala Glu Leu
```

-continued

130
Ser Pro Ala Ala Lys Thr Gly Lys Arg Lys Arg Ser Gln Met Leu

Phe Arg Gly

Formula II:

1                                          10
pyroGlu Asp Pro Tyr Val Lys Glu Ala Glu Asn Leu Lys Lys Tyr Phe 20                          30
Asn Ala Gly His Ser Asp Val Ala Asp Asn Gly Thr Leu Phe Leu 40
Gly Ile Leu Lys Asn Trp Lys Glu Glu Ser Asp Arg Lys Ile Met 50                                60
Gln Ser Gln Ile Val Ser Phe Tyr Phe Lys Leu Phe Lys Asn Phe 70
Lys Asp Asp Gln Ser Ile Gln Lys Ser Val Glu Thr Ile Lys Glu 80                              90
Asp Met Asn Val Lys Phe Phe Asn Ser Asn Lys Lys Lys Arg Asp 100
Asp Phe Glu Lys Leu Thr Asn Tyr Ser Val Thr Asp Leu Asn Val 110                         120
Gln Arg Lys Ala Ile His Glu Leu Ile Gln Val Met Ala Glu Leu Ser Pro Ala Ala Lys Thr Gly Lys Arg Formula III:

1                                          10
pyroGlu Asp Pro Tyr Val Lys Glu Ala Glu Asn Leu Lys Lys Tyr Phe 20                          30
Asn Ala Gly His Ser Asp Val Ala Asp Asn Gly Thr Leu Phe Leu 40
Gly Ile Leu Lys Asn Trp Lys Glu Glu Ser Asp Arg Lys Ile Met 50                                60
Gln Ser Gln Ile Val Ser Phe Tyr Phe Lys Leu Phe Lys Asn Phe 70
Lys Asp Asp Gln Ser Ile Gln Lys Ser Val Glu Thr Ile Lys Glu 80                              90
Asp Met Asn Val Lys Phe Phe Asn Ser Asn Lys Lys Lys Arg Asp 100
Asp Phe Glu Lys Leu Thr Asn Tyr Ser Val Thr Asp Leu Asn Val 110                         120
Gln Arg Lys Ala Ile His Glu Leu Ile Gln Val Met Ala Glu Leu Ser Pro Ala Ala Lys Thr Gly Lys Formula IV:

1                                          10
pyroGlu Asp Pro Tyr Val Lys Glu Ala Glu Asn Leu Lys Lys Tyr Phe 20                          30
Asn Ala Gly His Ser Asp Val Ala Asp Asn Gly Thr Leu Phe Leu 40
Gly Ile Leu Lys Asn Trp Lys Glu Glu Ser Asp Arg Lys Ile Met 50                                60
Gln Ser Gln Ile Val Ser Phe Tyr Phe Lys Leu Phe Lys Asn Phe 70
Lys Asp Asp Gln Ser Ile Gln Lys Ser Val Glu Thr Ile Lys Glu 80                              90
Asp Met Asn Val Lys Phe Phe Asn Ser Asn Lys Lys Lys Arg Asp -continued 100
Asp Phe Glu Lys Leu Thr Asn Tyr Ser Val Thr Asp Leu Asn Val 110                         120
Gln Arg Lys Ala Ile His Glu Leu Ile Gln Val Met Ala Glu Leu Ser Pro Ala Ala Lys Thr Gly, or Formula V:

1                                          10
pyroGlu Asp Pro Tyr Val Lys Glu Ala Glu Asn Leu Lys Lys Tyr Phe 20                          30
Asn Ala Gly His Ser Asp Val Ala Asp Asn Gly Thr Leu Phe Leu 40
Gly Ile Leu Lys Asn Trp Lys Glu Glu Ser Asp Arg Lys Ile Met 50                                60
Gln Ser Gln Ile Val Ser Phe Tyr Phe Lys Leu Phe Lys Asn Phe 70
Lys Asp Asp Gln Ser Ile Gln Lys Ser Val Glu Thr Ile Lys Glu 80                              90
Asp Met Asn Val Lys Phe Phe Asn Ser Asn Lys Lys Lys Arg Asp 100
Asp Phe Glu Lys Leu Thr Asn Tyr Ser Val Thr Asp Leu Asn Val 110                         120
Gln Arg Lys Ala Ile His Glu Leu Ile Gln Val Met Ala Glu Leu Ser Pro Ala Ala Lys Thr (wherein the abbreviations are commonly used for L-amino acids in the art)

In the above formula, a carbohydrate chain in the form of glycosylamine type of chain is coupled to either or both asparagines which are located at the twenty-fifth and ninety-seventh positions from the $NH_2$ terminus of the polypeptide chain.

In other words, the polypeptide chain shown by Formula II lacks 9 amino acids from the COOH terminus of the polypeptide chain shown by Formula I, and, similarly, the polypeptide chains shown by Formulas III, IV and V respectively lack 10, 11 and 12 amino acids from the COOH terminus of the polypeptide chain shown by Formula I. Specifically, it was also confirmed that the content of the polypeptide chain shown by Formula IV is relatively high, or about 50–80% based on molecular ratios of these polypeptide chains.

Experiment 2-3

Carbohydrate chain structure of human myelomonocyte IFN-gamma

The carbohydrate chain structure of a highly-purified human myelomonocyte IFN-gamma, prepared by the method in Example B-1(3), was studied.

Experiment 2-4(1)

Non-ionic saccharide and amino sugar composing carbohydrate chain of human myelomonocyte IFN-gamma In accordance with the method described in *European Journal of Biochemistry*, Vol.156, pp.651–654 (1986), a human myelomonocyte IFN-gamma prepared by the method in Example B-1(3) was subjected to methanolysis, and the resultant was trimethylcylylated, followed by feeding to gas-chromatography and determining a non-ionic saccharide in the IFN-gamma. Furthermore, a human myelomonocyte IFN-gamma was first hydrolyzed with methanesulfonic acid in accordance with the method described by R. J. Simpson et al., in *The Journal of Biological Chemistry*, Vol.251, No.7, pp.1936–1940 (1976), then fed to an amino acid analyzer to determine the amino sugar of human myelomonocyte IFN-gamma in accordance with the method described by A. M. Bella et al., in *Journal of Chromatography*, Vol.51, pp.314–315 (1970).

The results confirmed that both non-ionic saccharide and amino sugar consisted of D-mannose, D-galactose, L-fucose and N-acetyl-D-glucosamine in a molecular ratio of 3.00:2.16:0.82:3.94.

Experiment 2-4(2)

Arrangement and coupling mode of carbohydrate chain in human myelomonocyte IFN-gamma In accordance with the method described by S. Hase et al., in *The Journal of Biochemistry*, Vol.95, pp.197–203 (1984), a human myelomonocyte IFN-gamma prepared by the method in Example B-1(3) was subjected to hydrazinolysis and pyridylamination, and the resultant was then fed to gel chromatography to remove excessive amount of reagents to obtain a pyridylamino sugar chain, followed by determining an arrangement and a coupling mode of a carbohydrate chain in the human myelomonocyte IFN-gamma.

Anion exchange chromatography revealed that the pyridylamino sugar contained a monosialylated oligosaccharide and a disialylated oligosaccharide.

Furthermore, the pyridylamino sugar was digested with neuraminidase to obtain a disialylated pyridylamino sugar chain which was then fractionated according to molecular sizes with high-performance liquid chromatography. Each fraction was subjected to successive degradation using exoglycosidase to determine the arrangement of the carbohydrate chain of the human myelomonocyte IFN-gamma.

Furthermore, the pyridylamino sugar was fractionated with reverse-phase column chromatography, and the resultant fractions were respectively subjected to 500-MHz $^1$H-NMR spectroscopy to determine their coupling mode.

The results confirmed that the aforementioned polypeptide chain of the human myelomonocyte IFN-gamma was coupled to a carbohydrate chain shown by the following formula in the form of glycosylamine type of chain:

Formula VI:

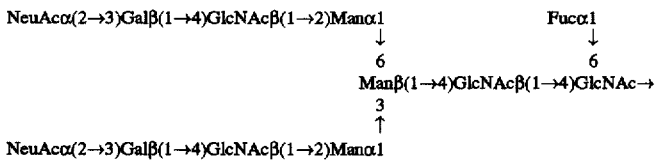

Formula VII:

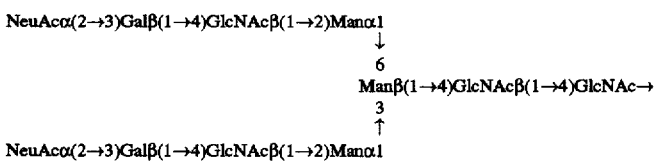

Formula VIII:

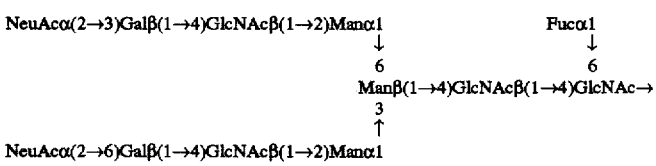

Formula IX:

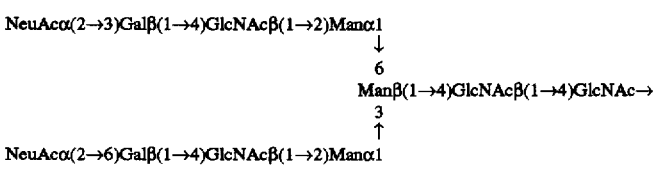

Formula X:

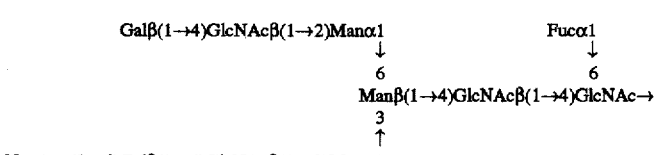

, or

Formula XI:

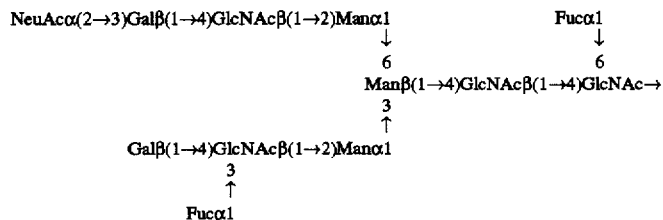

(wherein NeuAc, GlcNAc, Gal, Man and Fuc mean N-acetylneuraminic acid, N-acetyl-D-glucosamine, D-galactose, D-mannose and L-fucose respectively).

These structures of carbohydrate chains of human myelomonocyte IFN-gamma, which had not been found in IFN-alpha and IFN-beta, as well as in conventional HuIFN-gamma, for example, those derived from CHO cell and other cells, were revealed by the present invention.

Furthermore, the content of these novel carbohydrate chains was relatively high, i.e., about 50–80% based on a molecular ratio.

It was found that the present human myelomonocyte IFN-gamma also contained a small amount of carbohydrate chain which had been found in a CHO cell-derived HuIFN-gamma.

The results confirmed that the present human myelomonocyte IFN-gamma having a molecular weight of about 24,000 daltons has carbohydrate chains coupled to both asparagines which locate at the twenty-fifth and ninety-seventh positions with respect to the $NH_2$ terminus of the polypeptide chain, and the present human myelomonocyte IFN-gamma having a molecular weight of about 20,000 daltons has a carbohydrate chain which is coupled to one of the asparagines.

In conclusion, the present human myelomonocyte IFN-gamma derived from a human myelomonocyte is a novel HuIFN-gamma having a polypeptide chain shown by the following formula as the main structure:

Formula I:

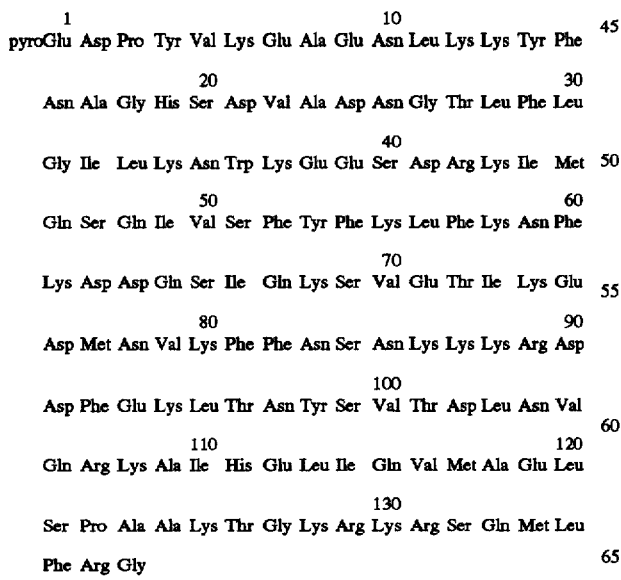

Formula II:

```
  1                                            10
pyroGlu Asp Pro Tyr Val Lys Glu Ala Glu Asn Leu Lys Lys Tyr Phe
                         20                              30
  Asn Ala Gly His Ser Asp Val Ala Asp Asn Gly Thr Leu Phe Leu
                                          40
  Gly Ile Leu Lys Asn Trp Lys Glu Glu Ser Asp Arg Lys Ile Met
                       50                              60
  Gln Ser Gln Ile Val Ser Phe Tyr Phe Lys Leu Phe Lys Asn Phe
                                       70
  Lys Asp Asp Gln Ser Ile Gln Lys Ser Val Glu Thr Ile Lys Glu
                       80                              90
  Asp Met Asn Val Lys Phe Phe Asn Ser Asn Lys Lys Lys Arg Asp
                                         100
  Asp Phe Glu Lys Leu Thr Asn Tyr Ser Val Thr Asp Leu Asn Val
                         110                            120
  Gln Arg Lys Ala Ile His Glu Leu Ile Gln Val Met Ala Glu Leu Ser Pro Ala Ala Lys Thr Gly Lys Arg
```

Formula III:

```
  1                                            10
pyroGlu Asp Pro Tyr Val Lys Glu Ala Glu Asn Leu Lys Lys Tyr Phe
                         20                              30
  Asn Ala Gly His Ser Asp Val Ala Asp Asn Gly Thr Leu Phe Leu
                                          40
  Gly Ile Leu Lys Asn Trp Lys Glu Glu Ser Asp Arg Lys Ile Met
                       50                              60
  Gln Ser Gln Ile Val Ser Phe Tyr Phe Lys Leu Phe Lys Asn Phe
                                       70
  Lys Asp Asp Gln Ser Ile Gln Lys Ser Val Glu Thr Ile Lys Glu
                       80                              90
  Asp Met Asn Val Lys Phe Phe Asn Ser Asn Lys Lys Lys Arg Asp
                                         100
  Asp Phe Glu Lys Leu Thr Asn Tyr Ser Val Thr Asp Leu Asn Val
                         110                            120
  Gln Arg Lys Ala Ile His Glu Leu Ile Gln Val Met Ala Glu Leu Ser Pro Ala Ala Lys Thr Gly Lys
```

Formula IV:

```
  1                                            10
pyroGlu Asp Pro Tyr Val Lys Glu Ala Glu Asn Leu Lys Lys Tyr Phe
                         20                              30
  Asn Ala Gly His Ser Asp Val Ala Asp Asn Gly Thr Leu Phe Leu
```

-continued

Gly Ile Leu Lys Asn Trp Lys Glu Glu Ser Asp Arg Lys Ile Met
         40
Gln Ser Gln Ile Val Ser Phe Tyr Phe Lys Leu Phe Lys Asn Phe
 50                              60
Lys Asp Asp Gln Ser Ile Gln Lys Ser Val Glu Thr Ile Lys Glu
                    70
Asp Met Asn Val Lys Phe Phe Asn Ser Asn Lys Lys Lys Arg Asp
         80                              90
Asp Phe Glu Lys Leu Thr Asn Tyr Ser Val Thr Asp Leu Asn Val
                    100
Gln Arg Lys Ala Ile His Glu Leu Ile Gln Val Met Ala Glu Leu
     110                         120
Ser Pro Ala Ala Lys Thr Gly, or

Formula V:

1                    10
pyroGlu Asp Pro Tyr Val Lys Glu Ala Glu Asn Leu Lys Lys Tyr Phe
              20                     30
Asn Ala Gly His Ser Asp Val Ala Asp Asn Gly Thr Leu Phe Leu -continued Gly Ile Leu Lys Asn Trp Lys Glu Glu Ser Asp Arg Lys Ile Met
         40
Gln Ser Gln Ile Val Ser Phe Tyr Phe Lys Leu Phe Lys Asn Phe
 50                              60
Lys Asp Asp Gln Ser Ile Gln Lys Ser Val Glu Thr Ile Lys Glu
                    70
Asp Met Asn Val Lys Phe Phe Asn Ser Asn Lys Lys Lys Arg Asp
         80                              90
Asp Phe Glu Lys Leu Thr Asn Tyr Ser Val Thr Asp Leu Asn Val
                    100
Gln Arg Lys Ala Ile His Glu Leu Ile Gln Val Met Ala Glu Leu
     110                         120
Ser Pro Ala Ala Lys Thr (wherein the abbreviations are commonly used for L-amino acids in the art).

wherein either or both of asparagines which locate at the twenty-fifth and ninety-seventh positions with respect to the NH$_2$ terminus of the polypeptide chain is coupled to a carbohydrate chain shown by Formula VI:

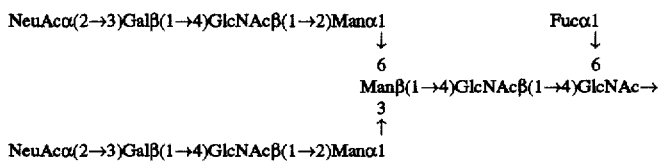

Formula VII:

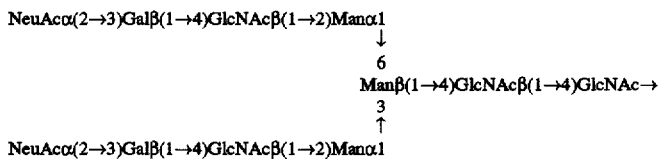

Formula VIII:

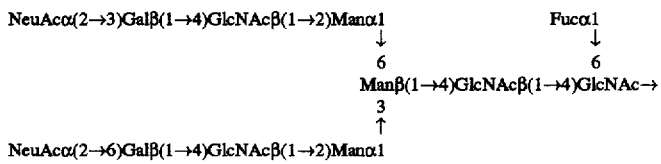

Formula IX:

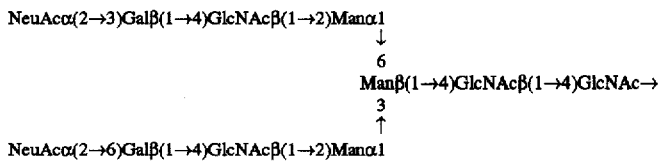

Formula X:

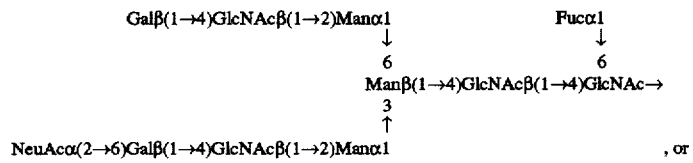

, or

Formula XI:

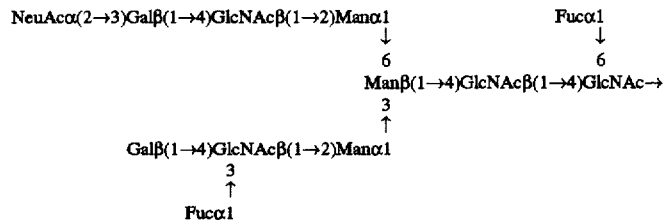

(wherein NeuAc, GlcNAc, Gal, Man and Fuc mean N-acetylneuraminic acid, N-acetyl-D-glucosamine, D-galactose, D-mannose and L-fucose respectively).

The product can be advantageously used as an effective component in therapeutic or prophylactic agents for vital diseases and malignant tumors, as well as a material for preparing HuIFN-gamma derivatives.

The following Experiments 3 are illustrative of preventing and treating HuIFN-gamma susceptive diseases using a human myelomonocyte IFN-gamma.

Experiment 3

Prophylactic and therapeutic effects of human myelomonocyte IFN-gamma on HuIFN-gamma susceptive diseases

Experiment 3-1

Virus inhibitory activity in vitro

A primary monolayer culture of human fetal lung in 6 cm Petri dish was added with a human myelomonocyte IFN-gamma prepared by the method in Example B-1(3) in an inoculum of 0.1, 1.0 or 10.0 units, and incubated in 5% $CO_2$ incubator at 37° C. for 20 hours. The resultant culture was added with either varicella-zoster virus or human cytomegalovirus in a dose that was capable of forming 100 plaques in the absence of human myelomonocyte IFN-gamma.

The virus inhibitory activity was determined with the decreasing rate of plaque number.

$$\text{Plaque reduction rate (\%)} = \frac{A-B}{A} \times 100$$

wherein A designates the plaque number with no addition of human myelomonocyte IFN-gamma; B, that with addition of human myelomonocyte IFN-gamma.

The results were as shown in Table V.

TABLE V

| Human myelomonocyte IFN-gamma (units) | Varicella-zoster virus | Cytomegalovirus |
|---|---|---|
| 0.1 | 11% | 10% |
| 1.0 | 54% | 49% |
| 10.0 | 93% | 88% |

These results confirmed that the human myelomonocyte IFN-gamma used in the invention was extremely inhibitory to the growth of pathogenic viruses.

Experiment 3-2

Treatment of malignant tumors with human myelomonocyte IFN-gamma

Experiment 3-2(1)

Cytostatic activity of human myelomonocyte IFN-gamma on malignant tumors in vitro An aliquot of RPMI 1640 medium supplemented with 15 v/v % fetal calf serum was added with a human myelomonocyte IFN-gamma prepared by the method in Example B-1(3) to a final concentration of 5, 50 or 500 units/ml, and the mixture was inoculated with a malignant human tumor cell to $5 \times 10^5$ cell/ml. The resultant was incubated in 5% $CO_2$ incubator at 37° C. for three days. As control, the same amount of a human myelomonocyte IFN-gamma preinactivated by 30-minute incubation at 100° C. was added to a fresh preparation of the same culture medium, and the mixture was treated similarly as above. After culture, the viable cell was stained with neutral red in accordance with the method as described in Applied Microbiology, Vol.22, No.4, pp.671–677 (1971). Thereafter, neutral red was eluted with acidified ethanol, and the number of viable cell was determined with the absorbance of the eluate at 540 nm.

Cytostatic rate (%) was determined with the following equation:

$$\text{Cytostatic rate (\%)} = \left(1 - \frac{A}{B}\right) \times 100$$

wherein A designates the number of viable cell in the test system, and B, that in the control.

The results were as shown in Table VI.

TABLE VI

| Human myelomonocyte IFN-gamma (unit/ml) | Tumor cell | | | |
|---|---|---|---|---|
| | KB | HEp-2 | KATO-II | P-4788 |
| 5 | 18% | 14% | 28% | 9% |
| 50 | 72% | 31% | 60% | 22% |
| 500 | 93% | 53% | 85% | 43% |

Note: KB cell is of human oral epidermoid carcinoma origin; HEp-2 cell, human larynx epidermoid carcinoma origin; KATO-II cell, human stomach carcinoma origin; and P-4788, human colon carcinoma origin.

These results confirmed that the human myelomonocyte IFN-gamma used in the invention was extremely inhibitory at a concentration of 5–500 units/ml to the growth of malignant tumor cells such as KB cell, HEp-2 cell, KATO-II cell and P-4788 cell.

Experiment 3-2(2)

Potentialization of cytostatic activity of other lymphokines by human myelomonocyte IFN-gamma in vitro The lymphokines used in this Experiment were human myelomonocyte IFN-gamma (5 units/ml), HuIFN-alpha (50 units/ml) and TNF (10 units/ml). The HuIFN-alpha and TNF were natural products derived from lymphoblastoid cells.

These lymphokines were tested for cytostatic rate (%) in accordance with the method in Experiment 3-2(1). The results were as shown in Table VII.

TABLE VII

| Lymphokine | Tumor cell | | | |
|---|---|---|---|---|
| | KB | HEp-2 | KATO-II | P-4788 |
| Human myelomonocyte IFN-gamma | 16% | 14% | 26% | 9% |
| HuIFN-alpha | 9% | 6% | 11% | 5% |
| T N F | 5% | 6% | 10% | 6% |
| Human myelomonocyte IFN-gamma plus HuIFN-alpha | 45% | 30% | 43% | 27% |
| Human myelomonocyte IFN-gamma plus T N F | 70% | 51% | 54% | 42% |
| Human myelomonocyte IFN-gamma, HuIFN-alpha plus T N F | 92% | 65% | 78% | 61% |

These results evidently confirmed that combination with human myelomonocyte IFN-gamma extremely enhanced the cytostatic effect of other lymphokines on malignant tumors and the enhancement was synergistic.

Experiment 3-2(3)

Potentialization of cytostatic activity of chemotherapeutics on malignant tumors by human myelomonocyte IFN-gamma in vitro One ml aliquots of a nutrient culture medium prepared in accordance with the method in Experiment 3-2(1) was inoculated with $10^6$ cells of a human malignant tumor cell, and the mixture was cultured for one day. The resultant culture was added with 50 units of a human myelomonocyte IFN-gamma prepared by the method in Example B-1(3) and/or 0.1 ml of saline containing a chemotherapeutic, and cultured at 37° C. for two days. As control, a saline free of human myelomonocyte IFN-gamma and chemotherapeutic was used. After the culture, the cytostatic rate (%) was determined in accordance with the method in Experiment 3-2(1). The concentration of the chemotherapeutics were as follows: nimustine hydrochloride (ACNU), $1.0 \times 10^{-6}$ g/ml; fluorouracil (5-FU), $1.5 \times 10^{-8}$ g/ml; doxorubicin (ADM), $1.0 \times 10^{-10}$ g/ml; mitomycin C (MMC), $2.5 \times 10^{-9}$ g/ml; and vincristine sulfate (VCR), $1.5 \times 10^{-10}$ g/ml.

The results were as shown in Table VIII.

TABLE VIII

| Chemotherapeutic | Human myelomonocyte IFN-gamma | Tumor cell | | | |
|---|---|---|---|---|---|
| | | HEp-2 | PC-9 | HLE | HeLa |
| — | + | 38% | 53% | 44% | 52% |
| ACNU | − | 4% | 2% | 5% | 5% |
| | + | 54% | 65% | 63% | 72% |
| 5-FU | − | 8% | 10% | 8% | 12% |
| | + | 67% | 68% | 71% | 70% |
| ADM | − | 13% | 6% | 7% | 17% |
| | + | 59% | 72% | 62% | 64% |
| MMC | − | 10% | 5% | 12% | 7% |
| | + | 61% | 64% | 65% | 62% |
| VCR | − | 5% | 8% | 10% | 10% |
| | + | 58% | 66% | 58% | 65% |

Note: (−) means with no addition; and (+) with addition. HEp-2 cell is of human larynx epidermoid carcinoma origin; PC-9, of human lung carcinoma origin; HLE, of human liver carcinoma; and HeLa, of human cervix epitheloid carcinoma origin.

These results evidently confirmed that human myelomonocyte IFN-gamma extremely enhanced the cytostatic activity of chemotherapeutics on malignant tumors and the enhancement was arithmetic or synergistic.

Experiment 3-2(4)

Cytostatic activity on malignant tumors in vivo

BALB/c nude mice were implanted at their dorsal area with a segment of human breast cancer tissue. From the time when the tumors grew to about 200 mm$^3$ the nude mice were injected once every day with one or more human myelomonocyte IFN-gamma prepared by the method in Example B-1(3), a lymphokine derived from human lymphoblastoid cell, and/or a chemotherapeutic in saline solution over a period of 20 days.

Thereafter, the nude mice were sacrificed, and the tumors were weighed.

As control, saline was injected similarly as above. The results were as shown in Table IX.

These results evidently confirmed that human myelomonocyte IFN-gamma extremely inhibited the growth of malignant tumors in vivo. The cytostatic activity was extremely enhanced to exert a strong antioncotic effect by combining one or more lymphokine(s) or chemotherapeutic(s).

TABLE IX

| Treatment | Dose/kg/day | Tumor (g) |
|---|---|---|
| Control | — | 10.8 ± 1.0 |
| Human myelomonocyte IFN-gamma | 50 units | 6.5 ± 0.9* |
| HuIFN-alpha | 500 units | 7.1 ± 0.8* |
| T N F | 100 units | 6.4 ± 0.5* |
| M M C | 1 mg | 5.1 ± 0.4* |
| Human myelomonocyte IFN-gamma plus HuIFN-alpha | 500 units 100 units | 4.6 ± 0.5* |
| Human myelomonocyte IFN-gamma plus T N F | 50 units 100 units | 4.3 ± 0.5* |
| Human myelomonocyte IFN-gamma plus M M C | 50 units 1 mg | 3.9 ± 0.4* |
| Human myelomonocyte IFN-gamma | 50 units | 2.7 ± 0.5* |

TABLE IX-continued

| Treatment | Dose/kg/day | Tumor (g) |
|---|---|---|
| HuIFN-alpha | 500 units | |
| plus T N F | 100 units | |
| Human myelomonocyte IFN-gamma | 50 units | 2.6 ± 0.6* |
| HuIFN-alpha | 500 units | |
| plus M M C | 1 mg | |

Note: The values were stochastically significant against the control at a significance level of 5%.

Experiment 3-2(5)

Acute toxicity

The acute toxicity of a human myelomonocyte IFN-gamma preparation obtained by the method in Example B-1(3) was tested using 20-day old mice.

The result confirmed that the toxicity of the human myelomonocyte IFN-gamma was extremely low, i.e. $10^9$ units or higher in terms of $LD_{50}$, when intraperitoneally injected.

The following Examples C are illustrative of preparing pharmaceutical composition containing as an effective ingredient the human myelomonocyte IFN-gamma prepared by the method according to the invention.

EXAMPLE C-1

Liquid medicine

A liquid medicine was prepared by dissolving in saline a human myelomonocyte IFN-gamma obtained by the method in Example B-1(3) to 500 units/ml.

The product in the form of nebula, collyrium, collunarium or collutorium is suitable for prophylactic and therapeutic agent for vital diseases such as epidemic conjunctivitis and influenza.

EXAMPLE C-2

Injection

A sold injection was obtained by dissolving in saline 100,000 units/ml of a human myelomonocyte IFN-gamma prepared by the method in Example B-2(3), sterilely filtering, distributing and lyophilizing 2 ml aliquots of the filtrate in vials, and sealing the vials.

The product is advantageously usable for prophylactic and therapeutic agent for vital diseases similarly as the product in Example C-1.

The product is suitable for prophylactic and therapeutic agent for malignant tumors such as breast cancer, lung carcinoma, liver carcinoma and leukemia; and immunopathies such as atopic allergy, pernicious anemia, articular rheumatism, and systemic lupus erythematosus.

The product is suitable as an enhancer for chemotherapeutics such as melphalan, methotrexate and ADM.

EXAMPLE C-3

Injection

To saline were added 10,000 units/ml of a human myelomonocyte IFN-gamma prepared by the method in Example B-3, 100,000 units/ml of natural lymphoblastoid HuIFN-alpha, and 100,000 units/ml of natural lymphoblastoid TNF, and the mixture was sterilely filtered and lyophilized similarly as in Example C-2 to obtain a solid injection.

The product is suitable for prophylactic and therapeutic agent for viral diseases.

The product is also suitable for prophylactic and therapeutic agent for malignant tumors such as breast cancer, lung carcinoma, liver carcinoma, stomach cancer and leukemia; and immunopathies such as atopic allergy, collagenasis, articular rheumatism, and systemic lupus erythematosus.

The product can be advantageously used to enhance the cytostatic activity of chemotherapeutics such as tegafur, MMC and VCR.

EXAMPLE C-4

Ointment

A human myelomonocyte IFN-gamma prepared by the method in Example B-1(3), and a natural lymphoblastoid HuIFN-alpha were kneaded together with a small amount of liquid paraffin in usual manner, and the mixture was added with white petrolatum to give human myelomonocyte IFN-gamma and HuIFN-alpha concentrations of 50,000 units/g and 500,000 units/g respectively.

The product is suitable for prophylactic and therapeutic agent for skin diseases such as herpes, skin carcinoma, and atopic dermatitis.

EXAMPLE C-5

Enteric coated tablet

In the preparation of conventional tablet using starch and maltose as vehicle, a human myelomonocyte IFN-gamma prepared by the method in Example. B-5 and a natural lymphoblastoid TNF were incorporated into the tablet in respective amount of 10,000 units per tablet (200 mg). The obtained tablets were then coated with methylcellulose phthalate.

The product is advantageously usable for prophylactic and therapeutic agent for vital disease such as those in small and large intestines, as well as that for malignant tumors such as colon carcinoma and liver carcinoma, and immunopathies such as atopic allergy, pernicious anemia, articular rheumatism, and systemic lupus erythematosus.

The product can be advantageously used to enhance the antioncotic activity of chemotherapeutics such as ADM, 5-FU and MMC.

As detailed heretofore, conventional process provides an insufficient HuIFN-gamma productivity and this renders industrial-scale production of HuIFN-gamma very difficult. While based on the finding that established human myelomono-cytes exert a superiorly high HuIFN-gamma producibility and produce a novel HuIFN-gamma, the present invention provides a novel human myelomonocyte IFN-gamma and a process thereof which is favorably practiceable on an industrial-scale.

The present invention also provides a process to prepare a monoclonal antibody using the human myelomonocyte IFN-gamma thus obtained, as well as providing a purification using the antibody and a prophylactic and therapeutic agent for HuIFN-gamma susceptive diseases. The agent is very effective to viral diseases, malignant tumors, rheumatism and immunopathies, treatment of which has deemed very difficult.

The present invention is a significant invention in the art. We claim:

1. A method for purifying a human myelomonocyte interferon-gamma, comprising:

propagating an established human myelomonocyte which produces human myelomonocyte interferon-gamma; and recovering the human myelomonocyte interferon-gamma by column chromatography using an antibody specific to human myelomonocyte interferon-gamma.

2. The method of claim 1, wherein said established human myelomonocyte is obtained by:

implanting an established human myelomonocyte capable of producing human myelomonocyte interferon-gamma in a non-human warm-blooded animal, or inoculating the established human myelomonocyte in a diffusion chamber placed inside or outside the body of a non-human warm-blooded animal; and allowing the established human myelomonocyte to proliferate while allowing it to receive the body fluid from the non-human warm-blooded animal.

3. The method of claim 1, wherein said antibody specific to human myelomonocyte interferon-gamma is obtained by:

propagating an established human myelomonocyte which produces myelomonocyte interferon-gamma;

recovering and purifying the interferon-gamma produced by said human myelomonocyte;

immunizing a non-human warm-blooded animal using the recovered and purified human myelomonocyte interferon-gamma as an antigen;

recovering an antibody producing cell from the animal;

fusing said antibody producing cell with a myeloma cell to produce hybrid cells;

selecting from said hybrid cells a hybrid cell capable of producing a monoclonal antibody specific to human myelomonocyte interferon-gamma; and culturing the hybrid cell to produce said monoclonal antibody specific to human myelomonocyte interferon-gamma.

4. The method of claim 1, wherein said established human myelomonocyte is contacted with an inducer after propagation.

5. The method of claim 4, wherein said inducer is a member selected from the group consisting of phytohemagglutinin, concanavalin A, pokeweed mitogen, lipopolysaccharide, lipid A, endotoxin, polysaccharide, bacteria, antigens and mixtures thereof.

* * * * *